United States Patent [19]

Wagner

[11] 4,303,829
[45] Dec. 1, 1981

[54] METHOD OF AND DEVICE FOR DETERMINING BODY CONTOURS FOR THE MEASUREMENT OF THE ABSORPTION DISTRIBUTION IN A SLICE OF THE BODY

[75] Inventor: Wolfgang Wagner, Hamburg, Fed. Rep. of Germany

[73] Assignee: U.S. Philips Corporation, New York, N.Y.

[21] Appl. No.: 83,195

[22] Filed: Oct. 9, 1979

[30] Foreign Application Priority Data

Oct. 14, 1978 [DE] Fed. Rep. of Germany ....... 2844927

[51] Int. Cl.$^3$ .............................................. A61B 6/00
[52] U.S. Cl. .................................................. 250/445 T
[58] Field of Search ........................... 250/445 T, 456

[56] References Cited

U.S. PATENT DOCUMENTS 4,034,224  7/1977  Heavens et al. ............... 250/445 T
4,114,040  9/1978  Hounsfield ..................... 250/445 T

Primary Examiner—Alfred E. Smith
Assistant Examiner—T. N. Grigsby
Attorney, Agent, or Firm—Thomas A. Briody; Robert T. Mayer; Jack E. Haken

[57] ABSTRACT

The invention relates to a method of determining the contour of a body slice which is irradiated in different directions situated in the slice in order to determine radiation absorption values. Taking into account the body contour, the absorption distribution of an examination zone situated fully or partly inside the slice can thus be reconstructed. To this end, the body is brought into contact with a confining member which contacts the body at different points which are situated in the irradiated plane. On each beam path which extends through one of the contact points and through the examination zone a contour point of the body is determined, the distance between this contour point and the contact point being determined as a value which corresponds to the quotient of the absorption values ($Q(p, v)$), each time associated with the beam path and obtained by measurement of the body absorption, and a predetermined, mean absorption coefficient ($\bar{\mu}$). The body contour can thus be at least approximately determined.

The reconstruction of the absorption distribution in the examination zone is realized so that the body zone extending outside the beam paths extending through the examination zone is divided into strips, the length of which is limited by the body contour, absorption data being assigned to the strips wherefrom, in conjunction with the absorption values, the absorption distribution in the examination zone is reconstructed.

10 Claims, 11 Drawing Figures

METHOD OF AND DEVICE FOR DETERMINING BODY CONTOURS FOR THE MEASUREMENT OF THE ABSORPTION DISTRIBUTION IN A SLICE OF THE BODY

The invention relates to a method of determining body contours for determining a radiation absorption distribution in a slice of a body, the body being irradiated in many directions in said slice in order to measure absorption values wherefrom the absorption distribution in the body slice is determined by means of the contour of the slice, and also relates to a device for performing the method.

A method of this kind is known from the article "Reconstruction from truncated scan data", by W. Wagner, published in Medita, special issue I/78. This method enables reconstruction of the absorption distribution of radiation, for example X-radiation, in an examination zone of, for example, a human body or organ which is situated in the irradiated plane (examination plane). The examination zone may be situated completely or partly within the irradiated body slice when, for example, only separate organs of the body are to be examined. This means that the examination zone may have a substantially smaller diameter than the positioning zone for the body in the plane. Contrary to the examination zone the body zone situated outside the examination zone is not completely irradiated in each direction, so that the radiation load for the body is reduced.

In order to prevent errors in the reconstructed absorption distribution of the examination zone, absorption data ($\bar{Q}(p, v)$) must be obtained in the body zones which are situated outside the examination zone and which are not completely irradiated by the measuring beams, said absorption data corresponding to the actual absorption data ($Q(p, v)$). For this purpose the body contour must be known. This contour is measured, as described in the previous German Patent Application P 28 02 593.6, by means of additional radiation sources which emit auxiliary radiation which is situated in the plane and which is substantially or completely absorbed by the body. The auxiliary radiation is directly emitted in the zone adjoining the examination zone, the auxiliary radiation then passing through the positioning zone. Part of the auxiliary radiation passes through the body and reaches an array of auxiliary detectors which are situated in the plane and by means of which the distance is determined between the auxiliary beams tangent to the body and the examination zone. By rotation of the auxiliary radiation source/auxiliary detector system around the body, a large number of auxiliary beams which are tangent to the body are generated in different directions. The contour of the body is then determined at least approximately as the envelope of the tangent auxiliary beams.

The additional absorption data required for the reconstruction of the absorption distribution of the examination zone are determined so that for each direction the zones of the body which are situated outside the examination zone and which are not irradiated by the measuring beams are subdivided into strips which extend at least approximately parallel to the measuring beams and whose width corresponds at least approximately to the paths of the measuring beams. The length of a strip is limited by the body contour. To each strip there is assigned a preselected absorption coefficient which relates to a uniform length and which represents at least approximately the mean body absorption. The absorption data which are valid for a given strip length are obtained by multiplication of the preselected absorption coefficient by each time the corresponding strip length.

The absorption data obtained, which are treated as if they were obtained by means of a measurement, and the absorption values are then used, as already described in said previous Patent Application P 28 02 593.6, to determine the absorption distribution with a substantially reduced radiation load for the body.

The installation of auxiliary radiation sources and auxiliary detectors for measuring the auxiliary beams in order to determine the body contour in tomography equipment, however, requires additional facilities which substantially increase the cost of such equipment.

The invention has for its object to provide a method of and a device for performing the method whereby the contour of a body can be determined without the installation of the required auxiliary devices in tomography apparatus making these apparatus more complex or substantially more expensive.

This object in accordance with the invention is realized in that the body to be examined is brought into contact with a confining member which contacts the body at a number of points which are situated at least approximately in the plane and which are predetermined or determined by measurement, on each beam path which extends through one of the contact points and through the examination zone there being determined a contour point, the distance between said contour point and the contact point being determined as a value which corresponds to the quotient ($L(p, v)$) of the absorption value $Q(p, v)$, each time associated with the beam path, and a predetermined, mean absorption coefficient ($\bar{\mu}$).

When the body to be examined is brought into contact with a confining member, the body to be examined contacts this confining member at a number of points (contact points) whose coordinates are given in advance on the confining member and are situated in the irradiated slice (examination plane) of the body. When the body is irradiated by parallel or fan-shaped measuring beams—both radiation geometries can be converted one into the other in known manner—a large number of measuring beams pass through each contact point in different directions situated in the examination plane and through the examination zone. On all beam paths extending through the contact points and followed by the measuring beams, whose width is determined by the width of the measuring paths, each time a further contour point is determined whose distance from the contact point in the direction of the body corresponds to a quotient ($L(p, v)$) which is formed from an absorption value determined for each beam path, divided by a mean, preselected absorption coefficient. The contour of the body to be examined is thus at least approximately determined by the contour points obtained.

Within the scope of the invention, the method can be used not only for simple bodies, for example, human bodies, but also for composite bodies, for example, the human body which is at least partly surrounded by radiation absorbing material.

Because the confining member can be comparatively simply brought into contact with the body to be examined—it is merely necessary to position the confining member in a defined position with respect to the reference system, for example, the centre of the examination zone—this method necessitates only small steps to be taken in the construction of tomography apparatus.

In a further version of the method in accordance with the invention, each time a further contour point is determined on the beam paths extending through the contour points thus obtained, starting from the contour points in the direction of the body, the distance between the further contour point and the original contour point being determined as a value which corresponds to the quotient of the absorption value each time associated with the beam path and a preselected, mean absorption coefficient.

The originally measured contour points represent new "quasi contact points" wherethrough each time a large number of beam paths extend which are situated in the plane. On each of these beam paths a further contact point is determined whose distance from the "quasi contact point" in the direction of the body again corresponds to the quotient $(L(p, v))$ determined for the relevant beam path. The number of contour points which at least approximately describe the body is thus substantially increased.

According to a further version in accordance with the invention, vectors which start from the centre of the examination zone and which reach as far as the contour points are averaged over preselected angular ranges in order to determine improved contour points, so that the contour of the body is more accurately determined.

To this end, vectors $(A(r, \phi))$ which reach from the centre of the examination zone to the contour points and which are situated in the examination plane are determined and averaged in predetermined angular sectors $(\Delta \phi)$ in known manner, so that each time for an angular sector a corrected contour point which represents the body contour is available.

A device for performing the method in accordance with the invention comprises at least one radiation source, the radiation of which completely passes through the body arranged on a patient table in the examination zone in different directions situated in the plane, each time along a number of at least approximately parallel extending beam paths, the radiation reaching a detector device which is arranged on the other side of the body in order to measure measuring values, and also comprises an electronic unit for determining the absorption distribution of the radiation by means of the measuring values and the contour points, there being provided a confining member which is made of a rigid material and which can be fixed on the examination table in a defined position, signal generators which are situated at least approximately in the plane and which generate an output signal when the body is contacted being arranged in predetermined positions on the confining member. The confining member is shaped so that it can be mounted on an examination table in a defined position, so that operational tomography apparatus can be equipped with this additional confining member.

The separate signal generators which are connected to the confining member are situated in predetermined positions on the side of the confining body which faces the body to be examined and also in the plane of examination. When the body is contacted, they each time supply an output signal wherefrom the location of the signal generator is determined.

In a further embodiment in accordance with the invention, the confining body consists of a flat, rectangular plate and two confining plates which are mounted to be pivotable around shafts provided on the former plate at opposite sides, the shafts extending perpendicularly to the plane.

Due to the plate-like construction of the confining body, this confining body can be particularly simply manufactured and positioned on an examination table of a tomography apparatus. The two confining plates, being made of a rigid material like the rectangular plate, moreover, increase the number of contact points in that these plates are arranged to contact the sides of the body to be examined. The body contour can thus be more accurately determined.

In a further embodiment in accordance with the invention, a plurality of series of signal generators which extend parallel to the surface are arranged on the confining body, so that when the body to be examined is irradiated in different examination planes which extend parallel with respect to each other, the confining body need not be moved with respect to the body.

In another embodiment in accordance with the invention, a device for performing the method comprises at least one radiation source, the radiation of which completely irradiates the body arranged on an examination table in the examination zone in different directions which are situated in the plane, each time along a number of at least approximately parallel beam paths, the radiation reaching a detector device in order to measure measuring values, said detector device being arranged on the other side of the body, and also comprises an electronic unit for determining the absorption distribution of the radiation by means of the measuring values and contour points, a confining body of predetermined geometry which is made of a rigid material being mounted on the examination table in a defined position, said confining body being covered with a flexible foil, between the foil and the confining member, there being provided a liquid whose absorption coefficient at least approximates that of the body.

A confining member of this kind enables a substantial increase of the number of contact points, because all delimitation points on the side of the confining member which faces the body may be considered as contact points for a given geometry of the confining body. To this end, the flexible foil which encloses the liquid in conjunction with the confining member is arranged against the body. The body to be examined thus constitutes, together with the liquid which at least partly encloses this body, a composite examination body corresponding to the body to be examined.

The drawing shows embodiments in accordance with the invention.

Figure 1:
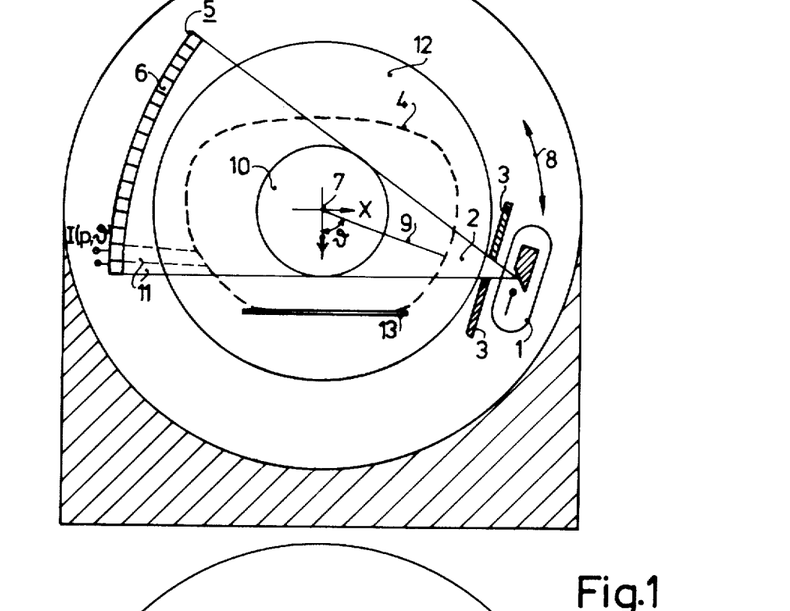
FIG. 1 shows an X-ray tomography apparatus.

FIG. 1 is a diagrammatic sectional view of an X-ray tomography apparatus which consists of a radiation source 1 for emitting a fan-shaped radiation beam 2 which extends in the plane of the section (plane of the drawing) representing the plane of examination and which is stopped by means of a lead aperture 3. The X-ray beam 2 passes through a body 4 to be examined and reaches a detector array 5 which consists of separate radiation detectors 6 which are adjacently arranged in the plane of examination. The system formed by the radiation source 1 and the detector array 5 is mounted to be rotatable in the direction of an arrow 8 around a central axis 7 which extends perpendicularly to the plane of examination the position of the system with respect to an orthogonal coordinate system X, Y in the plane of examination being given by an angle of rotation $v$ which is enclosed by the central ray 9 of the fan-shaped radiation beam 2 and the Y-axis. The origin of the coordinate system X, Y wherethrough the central axis 7 passes is at the same time the centre of the examination zone 10 of the X-ray tomography apparatus. This is the zone which is situated in the plane of examination and which is completely irradiated at each angle of rotation $v$ by measuring beams extending along beam paths 11, the width of the beam paths 11 being determined by the width of the detectors 6. For positioning the body 4 to be examined (denoted by broken lines), situated in a positioning zone 12 which concentrically envelops the examination zone 10, there is provided an examination table 13 which can be displaced perpendicularly to the plane of examination. The mechanical supporting system thereof has been omitted for the sake of clarity.

By changing the position of the body 4 inside the positioning zone 12, it can be achieved that the examination zone 10, the extent of which can be changed by adjustment of the aperture 3, covers various areas within the body 4 to be diagnosed. Obviously, there must be adequate clearance between the body 4 and the positioning zone 12 for this purpose.

Figure 2:
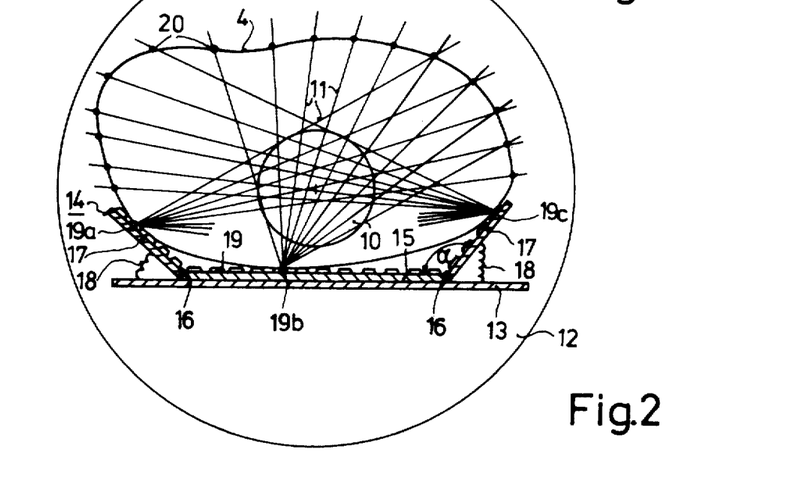
FIG. 2 shows a body to be examined, together with a confining member.

In FIG. 2, the body 4 to be examined is arranged on a confining member 14 which is mounted on the examination table 13 in a defined position. The confining member 14 is made of a rigid and at least approximately X-ray transparent material and consists of a rectangular plate 15 on which confining plates 17 are arranged to be pivotable each around a shaft 16 on opposite sides, said confining plates also having a rectangular shape and being pressed against the body 4 by means of springs 18. The angle α enclosed by the plate 15 and the confining plates 17 is measured by means of an angle detector (see FIG. 5). The shafts 16 extend perpendicularly to the plane of examination which is the plane of the drawing in the FIGS. 1 and 2. Instead of the springs 18, use can also be made of wedges of an elastic foam material, or the confining plates 17 can be interconnected by means of an elastic cord to be fastened across the body 4.

The confining member 14 accommodates separate signal generators 19 which are only diagrammatically shown and which are situated at predetermined locations in the plane of examination. When they contact the body 4, the signal generators 19 each time supply an output signal, for example, an electrical output signal, so that the signal generator 19 contacted by the body 4 is identified and hence its position in the plane of examination is determined. Obviously, the confining plates 17 must be pressed so firmly against the body 4 that the signal generators 19 provided thereon are activated.

When the body 4 contacts the confining member 14 at three contact points or at three signal generators 19a–c, as shown in FIG. 2, all beam paths are determined which extend through the signal generators 19a–c and the examination zone 10 for example, the beam paths 11. The individual beam paths 11 are described by calculated coordinates (p, $v$) of a flat, parallel radiation geometry, $v$ being the angle of rotation enclosed by an arbitrary beam path 11 and the Y-axis of the coordinate system XY, p representing the shortest distance between the beam path and the centre of the coordinate system XY. It is known that a parallel radiation geometry of this kind can be achieved by the resorting of beam paths of a fan-shaped radiation geometry (radiation beam 2).

From the measuring values I(p, $v$) obtained each time along the beam paths 11 by means of the detectors 6, absorption values Q(p, $v$) are then formed for each beam path 11 down to $$Q(p, v) = -\ln\{I(p, v)/I_o\} \quad (1)$$

Therein, Io is the radiation intensity which is not attenuated by the body 4 and which is measured by reference detectors.

The absorption values Q(p, $v$) each time obtained for a beam path 11 are divided by a preselected body absorption value $\bar{\mu}$ (mean absorption coefficient) which relates to a unit length, so that a quotient L(p, $v$) is formed which corresponds to an actual length. The body absorption value $\bar{\mu}$ is effectively that of water for the adjusted energy of the X-rays.

On each beam path 11, starting from the corresponding signal generators 19a–c (contact points) in the direction of the body 4, there is determined a point which represents a contour point 20 of the body 4 and whose distance from the relevant signal generator 19a–c each time corresponds to the quotient L(p, $v$). As is shown in FIG. 2, some of the contour points 20 are superposed. The more superpositions there are, that is to say the more signal generators 19 come into contact with the body 4, the more accurately the actual contour of the body 4 can be determined by the averaging of the contour points 20. The averaging of the contour points will be elaborated hereinafter.

Figures 3, 4:
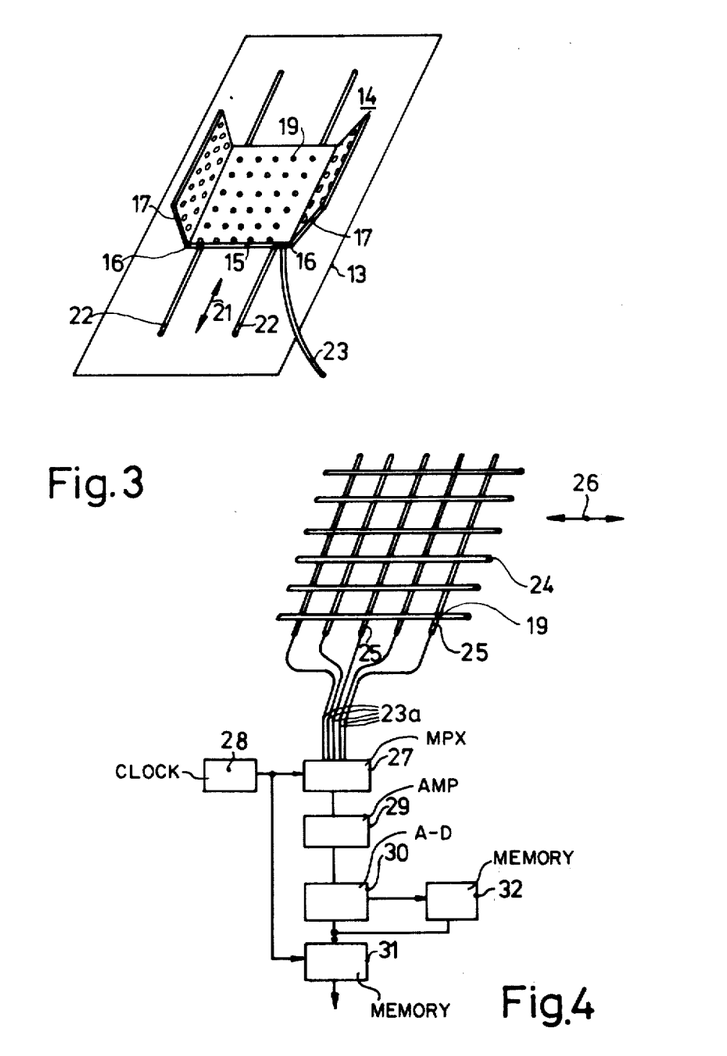
FIG. 3 is a perspective view of a confining member.
FIG. 4 shows a cross-conductor system for forming separate signal generators and an associated block diagram for processing the signals generated by the signal generators.

FIG. 3 is a perspective view of the confining body 14. The rectangular plate 15 and the confining plates 17 have a length of preferably approximately 10 cm in the longitudinal direction 21 of the examination table 13, so that several rows of signal generators 19 can be arranged on the confining body 14 parallel to the plane of examination. This is necessary because several, adjacent slices of the body are customarily successively irradiated. The distance between the rows of signal generators 19 then corresponds to the distance between the slices to be irradiated. The body 4 (patient), therefore, need not be displaced with respect to the confining body 14. On the other hand, the confining body 14 must be displaceable in the longitudinal direction 21 of the examination table 13 to enable the scanning of different areas of the body which are situated far apart.

To this end, rails 22 of a synthetic material are permanently mounted on the examination table 13; these rails are arranged in the longitudinal direction 21 and engage corresponding grooves in the lower side of the plate 15. The rails are provided with a graduation to enable reproducible adjustment of the confining member 14 by the operator.

The electrical signals from the signal generators 19 are applied, via a cable 23, to an electronic unit to be described hereinafter.

The examination table 13 may alternatively be constructed so that it is interrupted at the area of the plane of examination, so that the X-rays are not additionally attenuated by the table.

FIG. 4 shows, by way of example, an embodiment of the separate signal generators 19. They are defined as crosspoints of parallel transverse conductor tracks 24 and longitudinal conductor tracks 25 which extend at the same distance from each other and perpendicularly to each other. The transverse conductor tracks 24 extend parallel to the plane of examination and are vapour-deposited, like the longitudinal conductor tracks 25, each time on one side of a thin foil of a synthetic material, the foils being maintained at a distance from each other by a thin, X-ray transparent layer of a foam material (not shown), so that the track sides of the foils face each other. The layer of foam material is provided with holes at the area of the crosspoints (signal generators 19), so that when the signal generators 19 are exposed to pressure, direct contact occurs between the transverse conductor tracks 24 and the longitudinal conductor tracks 25 which are made, for example, of a material having only a low absorption coefficient for X-rays. For example, they may consist of aluminum tracks covered with a thin layer of gold.

The layer of foam material may also be formed to be continuous and it may have a low electrical conductivity which is substantially increased when exposed to pressure. Both embodiments of the foam layers enable a simple and cheap manufacture of the signal generators 19.

The location of the signal generators 19 on the plate 15 and the confining plates 17 is predetermined, as has already been stated, so that the output signals thereof are recorded for determining the location coordinates of the signal generators 19 which are actually contacted by the body 4. During operation, each time the transverse conductive track 24 situated in the plane of examination (denoted by the arrow 26) is connected to a power supply, whilst the longitudinal conductor tracks 25 are continuously sampled for the formation of (output) signals, via the lines 23a and the analog multiplexer 27 which is connected thereto and which is controlled by a clock generator 28. The signals are amplified in an amplifier 29 and are digitized in an analog-to-digital converter 30. In its simplest form, the analog-to-digital converter 30 is a threshold value amplifier. The digitized signals are stored in a memory 31.

For the signal generators 19 arranged on the plate 15, the signals present on the longitudinal conductor tracks 25 are simply associated with the location coordinates $x_i$ of the individual signal generators 19 situated on the X coordinate axis (FIG. 1). The $y_i$ coordinates of the signal generators accommodated on the plate 15 can all be considered to be constant, because the foam layer is very thin. For example, they are all situated at the same distance from the surface of the examination table 13, the height of which is described by the location coordinate y.

For determining the location coordinates of the signal generators 19 accommodated on the confining plates 17, moreover, the angle $\alpha$ between the plate 15 and the confining plates 17 must be determined.

Figure 5:
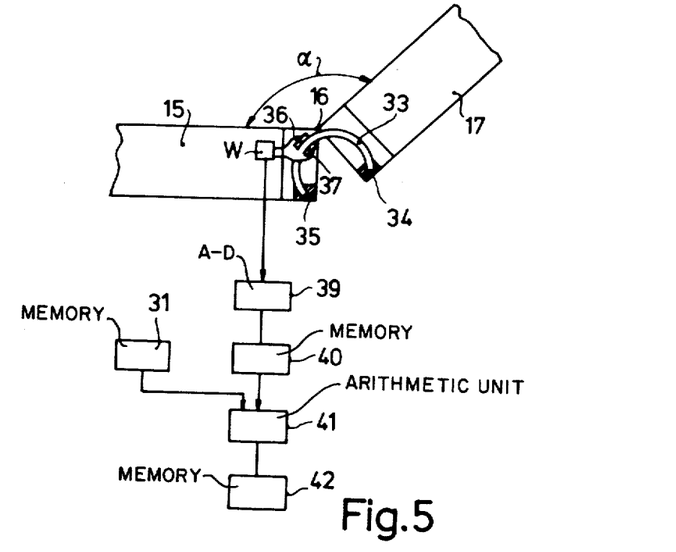
FIG. 5 shows a part of the confining body with an angle detector.

FIG. 5 shows an angle detector which consists of a flexible and curved rod 33 of a synthetic material which is journalled in movable bearings 34, 35. Above and below the rod 33 there is each time attached a strain-sensitive and pressure-sensitive resistance element 36, 37 by glueing, said elements being connected to form, in conjunction with two further pressure-independent resistors (not shown), an electrical resistance bridge W. When a confining plate 17 is pivoted around a shaft 16, the rod 33 is subjected to bending stress. The tensile forces or compression forces at its upper and lower side, cause a resistance variation of the elements 36 and 37 and hence an unbalance of the resistance bridge W. The angle-dependent electrical signals generated are applied to an amplifier and analog-to-digital converter 39. The relationship between the reistance unbalance and the angle $\alpha$ is stored in a memory 40. From the positions of the signal generators 19 on the confining plates 17, stored in the memory 31 (FIG. 4), and the angle $\alpha$, the arithmetic unit 41 calculates the corresponding angle-dependent coordinates $x_i(\alpha)$, $y_i(\alpha)$. In a memory 42, the coordinates $x_i$, $y_i$ of the signal generators 19 accommodated on the plate 15 as well as the coordinates $x_i(\alpha)$, $x_i(\alpha)$ of the signal generators 19 accommodated on the confining plates 17 are stored.

In order to increase the number of signal generators 19 contacted by the body 4, use can also be made of a foam layer which has a thickness of, for example, 5 cm and which is substantially transparent to X-rays and has a low conductivity, said foam layer being situated between the transverse conductor tracks 24 and the longitudinal conductor tracks 25. When the body 4 exerts a compression force, this foam layer is more or less compressed at different locations in the plane of examination, so that it contacts the body 4 over large areas. At the compressed locations, its electrical conductivity is increased, so that the signal generators 19 activated by the body 4 generate signals which are dependent of the compression of the foam layer or of the distance between the deformed surface thereof and a reference system, for example, the examination table 13.

The coordinates $x_i$, $y_i$ of the signal generators 19 on the plate 15 and the coordinates $x_i(\alpha)$, $y_i(\alpha)$ of the signal generators on the confining plates 17 should then be corrected accordingly. To this end, the relationship between the compression of the foam layer (or the distance between the surface thereof and the table top 13) and its electrical conductivity is stored in a memory 32 (FIG. 4). The digital output values of the analog-to-digital converter 30, being dependent of the pressure, are then additionally used for addressing in the memory 32, the distance found at each address also being stored in the memory 31.

The method will be described in detail with reference to FIG. 6 which shows a block diagram. The measuring values I(p, v) (intensities), or the reference intensity Io, measured by means of the detectors 6, are subjected to logarithmation in a logarithmation unit 43 which at the same time forms absorption values Q(p, v) which are stored in a memory 44. These absorption values $\overline{Q}(p, v)$ are used at a later stage for reconstructing the absorption distribution $\mu(x,y)$ in the examination zone 10 in the central computer 45, said distribution being displayed on the monitor 46.

For each of the coordinates $x_i$, $y_i$, $x_i(\lambda)$, $y_i(\lambda)$ of the signal generators 19 contacted by the body 4, stored in the memory 42, a first arithmetic unit 47 fetches the beam paths 11 extending therethrough and the absorption values Q(p, v) associated with the beam paths 11 and stored in the memory 44. From these absorption values Q(p, v), a second arithmetic unit 48 calculates the quotients L(p, v) and therefrom the contour points 20 of the body 4, as has already been described.

In a third arithmetic unit 49, further contour points 20 are determined in order to obtain a uniform distribution along the body contour. To this end, the contour of the body 4 is described, as shown in FIG. 7, by polar coordinates (r, $\phi$). The centre of the polar coordinate system then corresponds to the origin of the coordinate system XY. In FIG. 7, a beam path 11 extends, for example, through the coordinates $x_i(\alpha)$, $y_i(\alpha)$ of a signal generator 19 contacted by the body 4, on the beam path 11 there being fixed a contour point P(r, $\phi$) of the body 4 whose distance from the signal generator 9 corresponds to the quotient L(p, v). For a central vector A(r, $\phi$) which extends from the centre of the polar coordinate system, being at the same time the centre of the examination zone 10, to the contour point P(r, $\phi$), the following is applicable when the $i^{th}$ beam path 11 is oconcerned:

$$P_i = r \cos(v - \phi) \quad (2)$$

In conjunction with the determined quotient $L(p_i, v)$ it follows that:

$$r^2 = x_i^2(\alpha) + y_i^2(\alpha) + 2L(p_i, v) \cdot B \quad (3)$$

where $$B = \{x_i(\alpha) \cos(v + 90°) + y_i(\alpha) \cdot \sin(v + 90°)\} \quad (4)$$

and $$\phi = \arccos(p_i/r) + v \quad (5)$$

When the values $r(\phi)$ for all vectors A(r, $\phi$) thus found are plotted versus the angle $\phi$ in a diagram as shown in FIG. 8, a distribution of discrete values $r(\phi)$ is obtained which is more dense in some parts of $\phi$ than in other parts. In order to increase the uniformity of the distribution of the contour points along the body contour, separate values $r(\phi)$ are selected from the densely occupied parts of $\phi$ and their coordinates $x_p$, $y_p$ in the coordinate system XY are calculated. These coordinates are applied to the first arithmetic unit 47 (FIG. 6), so that further contour points 20 can be determined in the described manner. If necessary, this step may be repeated.

Figure 6:
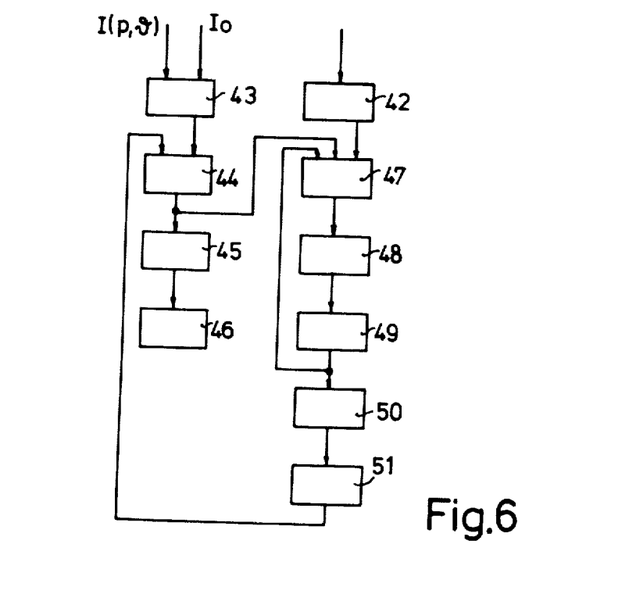
FIG. 6 shows a block diagram of an electronic unit for performing the method.
Figures 7, 8, 11:
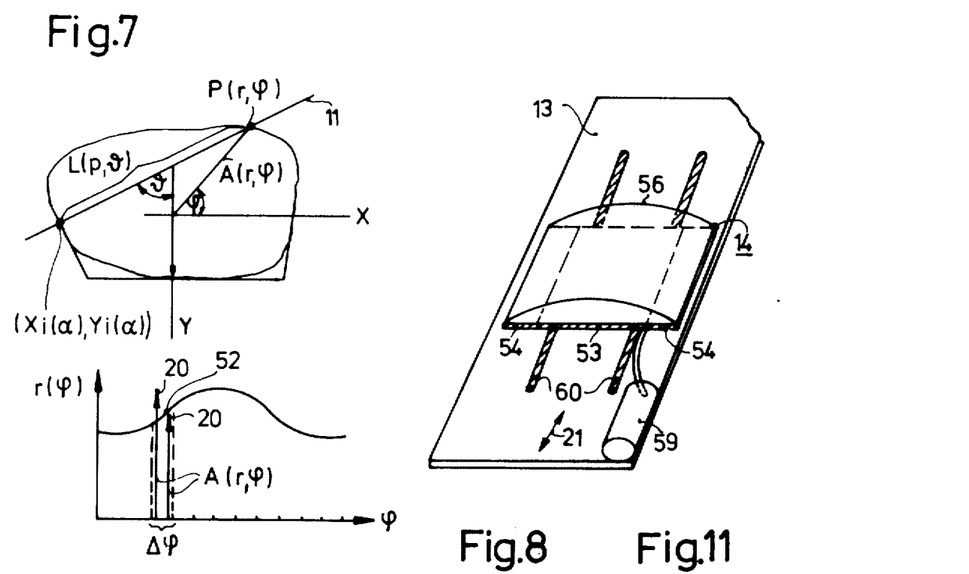
FIG. 7 shows a body slice situated in the examination plane.
FIG. 8 shows a diagram of the vectors extending from the centre of the examination zone to the contour points in dependence of an angle φ situated in the plane of examination for determination of corrected contour points.
FIG. 11 is a perspective view of a confining member covered by a flexible foil.

Subsequently, improved contour points 52 are determined by means of a fourth arithmetic unit 50 as shown in FIG. 6, in that the contour points 20 (FIG. 8) situated in separate, limited angular sections $\alpha\phi$ are averaged over the entire angle $\phi$. The angular sections amount to, for example, one degree.

A fifth arithmetic unit 51 as shown in FIG. 6 then produces, on the basis of the determined contour of the body 4 and in the described manner, the absorption data $\overline{Q}(p, v)$ which are also applied to the memory 44 for determining a reconstruction image of the examination zone 10.

Figure 9:
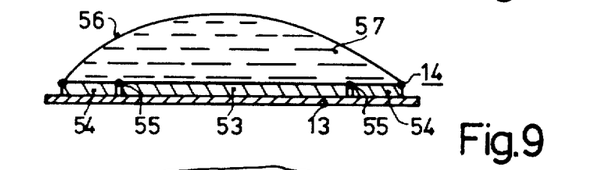
FIG. 9 is a sectional view in the plane of examination of a confining member covered by a flexible foil.
Figure 10:
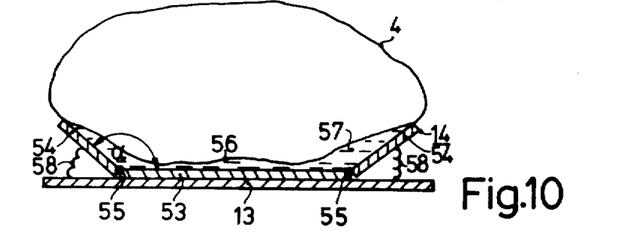
FIG. 10 is a sectional view in the plane of a confining member which is covered with a flexible foil and on which a body to be examined is arranged.

FIGS. 9 to 11 show a further embodiment of a confining member 14. FIG. 9 is a sectional view in the examination plane of a confining member 14 which can be arranged on the examination table 13 in a defined manner and which is shown in the no-load condition. It is made of a synthetic material which is substantially transparent to X-rays and consists of a thin, rectangular supporting plate 53 with two rectangular side plates 54 which are arranged to be pivotable around a shaft 55 on opposite sides of the supporting plate 53. The shafts 55 extend perpendicularly to the plane of examination which is the plane of the drawing. The confining member 14 is covered by a flexible foil 56, a liquid 57 being provided between the foil 56 and the confining member 14, the absorption coefficient of this liquid corresponding to the mean absorption coefficient of the body 4 (FIG. 10). Water is preferably used as the liquid 57. The foil 56 is tensioned so that it has an approximately cushion-shaped cross-section.

A body 4 to be examined is arranged on the confining member 14 in FIG. 10. The side plates 54 are pressed against the body 4 as far as possible, for example, by means of springs 58. The foil 56 then contacts the body 4; the liquid 57 can then flow back to a buffer container 59 (FIG. 11) which is not situated in the path of the X-rays. The liquid 57 and the body 4 together form a composite examination body which has an almost uniform composition in respect of the X-rays and which intimately contacts the confining member 14. Because the confining member 14 extends in the plane of examination—the angle $\alpha$ between the side plates 54 and the supporting plate 53 is determined in the manner already described with reference to FIG. 5—all pointed on the confining member may be considered to be contact points $x_i$, $y_i$ and $x_i(\alpha)$, $y_i(\alpha)$. Thus, a substantially larger number of contour points 20 of the body 4 can be determined in the described manner.

FIG. 11 is a perspective view of the confining member 14. This member has a length of preferably 40 cm in the longitudinal direction, a central zone of 30 cm being provided for use in the plane of examination. This is necessary when several parallel slices of the body 4 are successively irradiated, without the position of the body having to be changed in the meantime. The confining member 14 is also adjustable in the longitudinal direction 21.

To this end, rails 60 of a synthetic material are rigidly mounted on the examination table 13, the confining member 14 sliding on said rails by way of corresponding grooves. The rails 60 are provided with a scale graduation in order to enable reproducible adjustment of the confining member 14.

The geometry of the confining member 14 can also be adapted to the section of the body 4 situated in the plane of examination; for example, it may be shaped as a shell so that a confining member 14 without moving parts (for example, side plates 54) is obtained.

It is to be noted that the devices in accordance with the invention are also suitable for use in other X-ray tomography devices, for example, tomography apparatus which comprise, contrary to FIG. 1, stationary detectors which are situated in the plane of examination and which surround the examination zone, for example, in a circular manner.

What is claimed is:

1. In the method for determining a radiation absorption distribution in a plane slice of a body, comprising the steps of irradiating the body in many directions along a plurality of paths in the plane to measure absorption values and calculating the absorption distribution in the slice from the measured absorption values and data describing the contour of the slice, an improved method for determining the contour of the slice which comprises the steps of:

bringing the body into contact with a confining member which contacts the body at a plurality of contact points, situated at least approximately in the plane, the location of which are predetermined or are determined by measurement; and determining the location of first contour points defined by the intersection of the contour with each of a plurality of beam paths which extend through one of the contact points and through an examination zone, the distance between each contour point and a contact point being a value which corresponds to the quotient of the absorption value measured along the associated beam path and a predetermined mean absorption coefficient.

2. A method as claimed in claim 1 further comprising the steps of determining the location of further contour points on further beam paths which extend through a first contour point, the distance between the first contour point and the further contour point being the quotient of the absorption coefficient measured along the associated beam path and a preselected mean absorption coefficient.

3. A method as claimed in claim 1 further comprising the step of determining improved contour points by averaging vectors, which extend from the center of the examination zone to the contour points, over preselected annular sections.

4. A device for determining a radiation absorption distribution in a planar slice of a body comprising:

an examination table for supporting the body;
radiation source means for radiating the slice of the body with radiation from different directions in the plane;
radiation detector means disposed on an opposite side of the body from the radiation source means for measuring radiation which passes through the body and determining measuring values therefrom; and
means for calculating the absorption distribution of the radiation in the slice from the measuring values and from signals representing the locations of contour points which define the position of the periphery of the slice wherein, as an improvement,
the device further comprises rigid confining means which are secured in a defined position on the examination table and which include signal generators in predetermined positions, which are at least approximately in the plane of the slice, which generate output signals when they contact the body.

5. A device as claimed in claim 4 wherein the confining means comprise:

a first flat rectangular plate;
two confining members, each pivotably attached to an opposite edge of the first plate, for rotation about pivot axes which extend transverse to the plane of the slice.

6. A device as claimed in claim 5 wherein each confining member further includes a plurality of arrays of signal generators which arrays extend parallel to the plane of the slice.

7. A device as claimed in claims 4, 5, or 6 wherein each of the confining means comprises:

a thin foam layer;
first and second foils of a synthetic material disposed on opposite sides of the foam layer; a plurality of first conductor tracks, spaced at equal intervals and extending perpendicular to the plane of the slice on the inner side of the first foil and
a plurality of second conductor tracks, spaced at equal intervals and extending perpendicular to the first conductor tracks, disposed on the inner side of the second foil, the foam layer defining holes adjacent the cross points of the first and second conductor tracks which enable contacting of those tracks when the foil is compressed.

8. A device as claimed in claim 7 wherein the local electrical conductivity of the foam layer is dependent on the pressure applied thereto.

9. A device as claimed in claim 7 wherein the first conductor tracks and the second conductor tracks comprise a metal, having a low absorption coefficient for x-rays, which is vapor deposited on the inner sides of the respective foils.

10. A device as claimed in claim 4 further comprising a flexible foil which covers the confining means and a liquid, whose absorption coefficient substantially corresponds to that of the body, disposed between the foils and the confining means.

* * * * *